US00PP31052P2

(12) United States Plant Patent
Van Swieten

(10) Patent No.: US PP31,052 P2
(45) Date of Patent: Nov. 12, 2019

(54) ***PHALAENOPSIS* ORCHID PLANT NAMED 'PHALVAPYH'**

(50) Latin Name: ***Phalaenopsis* hybrid**
Varietal Denomination: PHALVAPYH

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,852

(22) Filed: May 8, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 6/62
See application file for complete search history.

(56) References Cited

PUBLICATIONS

Upov Pluto Plant Variety Database Mar. 29, 2019, retrieved on Apr. 9, 2019, retrieved from the Internet at https://www3.wipo.int/pluto/user/en/index.jsp, one page. (Year: 2019).*
EU Community Plant Variety Rights Application No. 2017/1130, Application n°A201701179, filed Apr. 25, 2017, 8 pages.
EU Community Plant Variety Office Official Gazette, Mar. 2017, Jun. 15, 2017, cover page and pp. 37, 57.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALVAPYH', particularly characterized by having light purple flowers with white centers and red-purple lips, 1 to 2 peduncles that are long and sturdy, leaves that are narrow obovate, and is propagated by meristem tissue culture, is disclosed.

3 Drawing Sheets

Genus and species: *Phalaenopsis* hybrid.
Variety denomination: 'PHALVAPYH'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALVAPYH'.

The new *Phalaenopsis* plant is a product of a planned breeding program conducted by the inventor in Bleiswijk, The Netherlands. The objective of this breeding program was to create a new *Phalaenopsis* plant with attractive light purple flowers with white centers and red-purple lips, suitable for potted plant production.

The new *Phalaenopsis* plant 'PHALVAPYH' is a result of cross-pollination made by the inventor in April 2007 in Bleiswijk, The Netherlands of the proprietary female, or seed parent, *Phalaenopsis* hybrid '22791-04' (unpatented) with the proprietary male, or pollen parent, *Phalaenopsis* hybrid '14261-01' (unpatented).

The new *Phalaenopsis* was selected by the inventor as a single plant within the progeny of the stated cross-pollination in a controlled greenhouse in Bleiswijk, The Netherlands in April 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALVAPYH' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALVAPYH' as a new and distinct variety of *Phalaenopsis* plant.

1) Light purple flowers with white centers and red-purple lips;
2) 1 to 2 peduncles;
3) Peduncle is long and sturdy; and
4) Shape of the leaf is narrow obovate.

DESCRIPTION OF THE PHOTOGRAPHS

This new *Phalaenopsis* plant is illustrated by the accompanying photographs which show the overall plant habit including blooms, bud and foliage of the plant; the colors shown are as true as can be reasonably obtained by conventional photographic procedures. The photographs were taken in a greenhouse in Bleiswijk, The Netherlands, from 50-week old plants in March 2018. Colors in the photographs may differ from the color values cited in the detailed botanical description, which accurately describe the actual colors of the new variety.

DESCRIPTION OF THE NEW VARIETY

Figure 1:
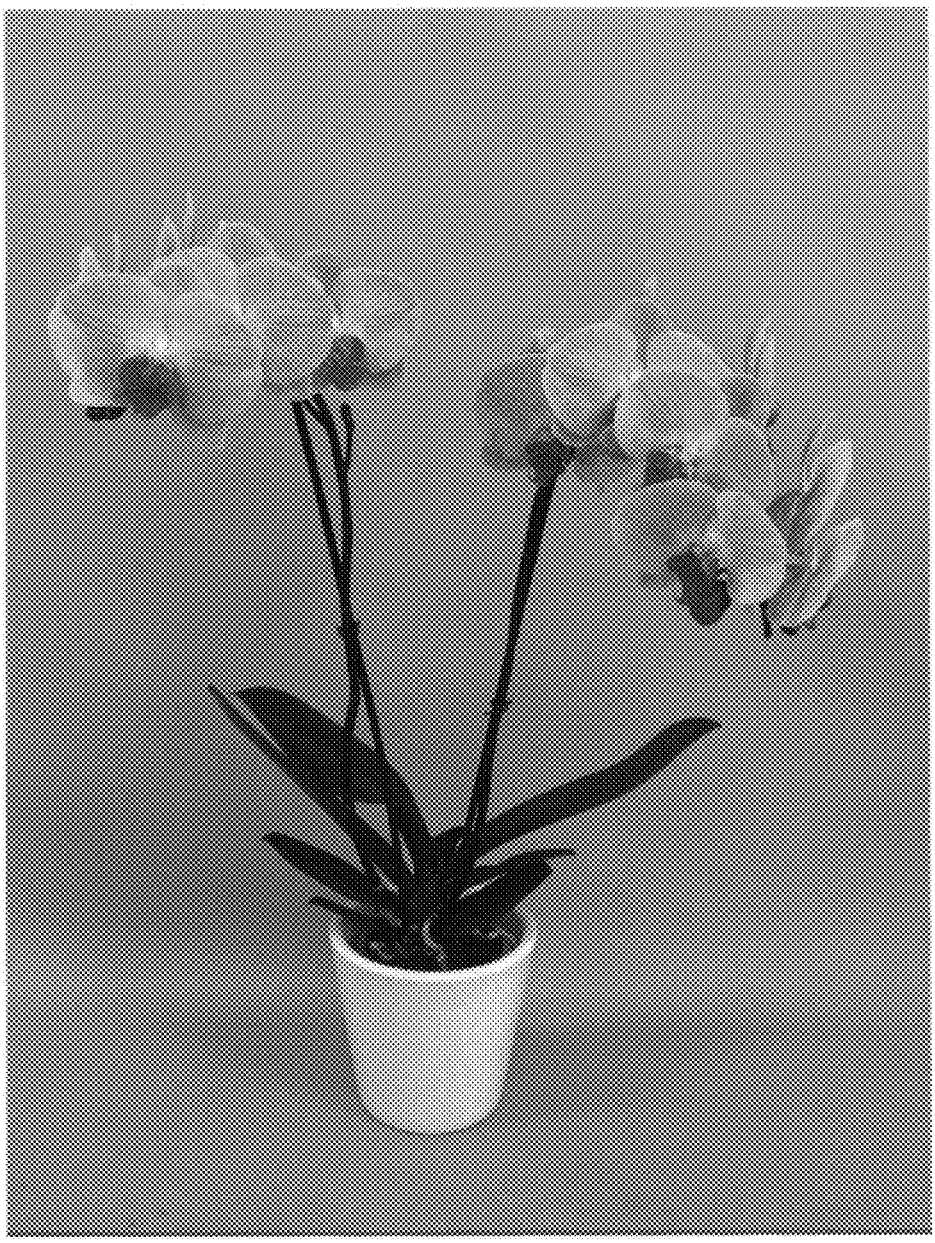
FIG. 1 shows the overall plant habit, including blooms, bud and foliage of 'PHALVAPYH'.
Figure 2:
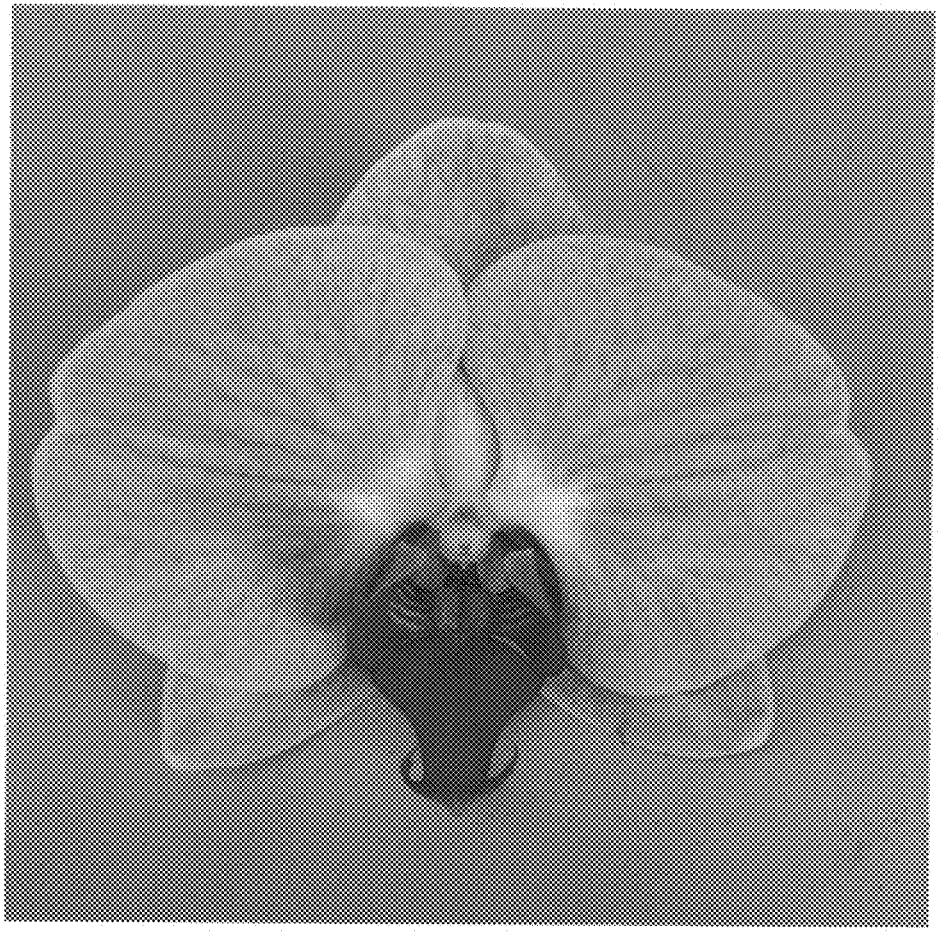
FIG. 2 shows a close-up of a flower of 'PHALVAPYH'.
Figure 3:
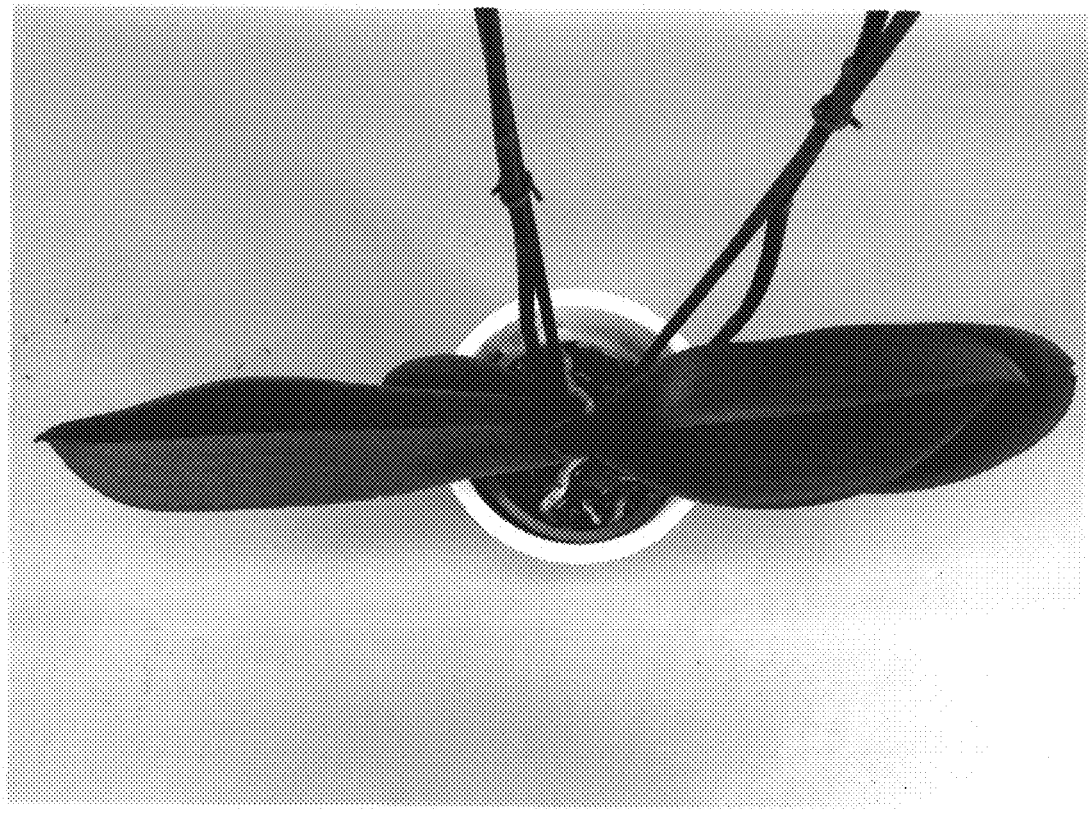
FIG. 3 shows an overhead view of the leaves of 'PHALVAPYH'.

The following detailed description sets forth the distinctive characteristics of 'PHALVAPYH'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in March 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in a 12 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALVAPYH'.

Parentage:

*Female parent*.—*Phalaenopsis* cultivar '22791-04' (unpatented).

*Male parent*.—*Phalaenopsis* cultivar '14261-01' (unpatented).

Propagation:

*Type*.—Meristem tissue culture.

Roots:

*Root description*.—Greyed-green colored roots (between RHS 190B and 190C) with branching lateral roots having dark red (RHS N79C) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Standard, green leaves, raceme to panicle.

*Height* (*from soil level to top of inflorescence*).—Approximately 55.0 cm to 60.0 cm.

*Width* (*measured from leaf tips*).—About 34.0 cm to 37.0 cm.

*Vigor*.—Moderate.

Leaves:

*Mature leaves*.—Quantity per plant: 6 to 8 leaves are produced before flowering. Length (fully expanded): 18.0 cm to 23.0 cm. Width: 6.0 cm to 8.0 cm. Shape: Narrow obovate. Base shape: Moderately elongated. Apex: Acute unequal. Leaf blade angle with the petiole (measured from the horizontal position): Between 30 degrees and 45 degrees. Leaf margin: Entire. Color: Upper surface: RHS 147A. Lower surface: RHS 147B with dark red (RHS 187A) margin toward the tip. Texture (both upper and lower surfaces): Rough. Thickness: 2.0 mm to 2.3 mm. Venation: Pattern: Parallel. Color of the midvein: Upper surface: RHS 147A. Lower surface: RHS 147B.

Peduncle:

*Quantity per plant*.—1 to 2.

*Number of flowers per peduncle*.—11 to 15.

*Length*.—55.0 cm to 60.0 cm.

*Diameter*.—5.0 mm to 7.0 mm.

*Strength*.—Strong.

*Aspect*.—Upright to slightly pendant.

*Texture*.—Smooth.

*Color*.—Mix of brown (RHS 200A) and green (RHS 147B).

*Internode length*.—3.0 cm to 4.0 cm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 210.0 mm to 230.0 mm.

*Flowering time*.—First flowers can be expected 10 to 11 months after planting in a 12 cm (diameter) pot.

*Flower*.—Height: 73.0 mm to 78.0 mm. Diameter: 95.0 mm to 100.0 mm. Depth of lip: 29.0 mm to 31.0 mm.

*Flower longevity*.—On the plant: 9 to 12 weeks.

*Fragrance*.—Absent.

*Flower bud*.—Average size: Medium to large. Length: 24.0 mm to 26.0 mm. Width: 19.0 mm to 21.0 mm. Shape: Egg shaped. Color: Slightly light green (RHS 146D) at the base; purple-red (RHS N77B and slightly RHS N79C) toward the tip.

*Petals*.—Arrangement: Open/free to touching. Shape: Semi-circular. Apex: Emarginated asymmetric. Margin: Entire. Length (from base to tip): 44.0 mm to 46.0 mm. Width: 56.0 mm to 58.0 mm. Color (when fully opened): Upper surface: Basic color: Light purple (RHS 76B). Over color: White (RHS NN155C) at the base; purple-pink (RHS N78C). Stripes: Amount: Medium. Spots: None. Netting: None. Lower surface: Basic color: Light purple (RHS 76C). Over color: Purple-pink (RHS N78C).

*Dorsal sepal*.—Shape: Broad elliptic. Apex: Rounded to slightly emarginated. Margin: Entire. Length (from base to tip): 44.0 mm to 46.0 mm. Width: 36.0 mm to 38.0 mm. Color (when fully opened): Upper surface: Basic color: Light purple (RHS 76B). Over color: Purple-pink (RHS N78C). Stripes: Amount: Medium. Color: RHS N78C. Spots: None. Netting: None. Lower surface: Basic color: Light purple (RHS 76A). Over color: Purple-pink (between RHS N78B and N78C); red-purple (RHS 72B) at the base.

*Lateral sepals*.—Shape: Ovate. Apex: Obtuse asymmetric. Margin: Entire. Length (from base to tip): 44.0 mm to 46.0 mm. Width: 29.0 mm to 31.0 mm. Color (when fully opened): Upper surface: Basic color: Light purple (RHS 76B). Over color: Light green (between RHS 145C and 145D) at the base and slightly white (RHS NN155C) with small red region (RHS 184B); red-purple (RHS N78D) toward the margin. Stripes: Amount: Medium. Color: RHS N78C. Spots: None. Netting: None. Lower surface: Basic color: Light purple (RHS 76A). Over color: Light green (RHS 146D) at the base; purple-pink (RHS N78C) with reddish purple stripes (between RHS 72A and 72B) toward the margin.

*Labellum* (*lip*).—Whiskers: Present. Length of whiskers: 9.0 mm to 11.0 mm. Color of whiskers: Reddish purple (RHS N78A). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 21.0 mm to 23.0 mm. Width: 14.0 mm to 16.0 mm. Color: White (RHS NN155B) at the base; red stripes and red region (RHS 60A) toward one margin; reddish purple (between RHS N78A and N78B) toward edge.

*Apical lobe*.—Shape: Triangular. Margin: Entire. Length: 23.0 mm to 25.0 mm. Width: 19.0 mm to 21.0 mm. Color: Upper surface: Slightly yellow (RHS 9A) at the base; dark red (RHS 59A) and red-purple (RHS N78A) toward the tip. Lower surface: Red-purple (RHS N78B) in the middle; dark purple (RHS N78A) toward the edge with an edge of dark red (RHS 59A).

*Callus*.—Average size: Medium. Height: 6.0 mm to 7.0 mm. Length: 5.0 mm to 6.0 mm. Width: 4.0 mm to 5.0 mm. Color: Yellow (RHS 15A) dotted (RHS 181A).

Reproductive organs:

*Column*.—Length: 8.0 mm to 10.0 mm. Diameter: 5.3 mm to 5.5 mm. Color: Purple-pink (RHS N78C).

*Pollinia*.—Quantity: 2. Diameter: 0.7 mm to 0.9 mm. Color: Orange (RHS 25A).

*Ovary*.—Length: 10.0 mm to 12.0 mm. Diameter: 2.4 mm to 2.6 mm.

*Pedicel*.—Length: 31.0 mm to 34.0 mm. Diameter: 2.7 mm to 2.9 mm. Color: Light green (RHS 146D) and very light purple (RHS 76D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALVAPYH' differs from female parent plant '22791-04' (unpatented) in that 'PHALVAPYH' has an acute leaf apex, light purple flowers and a dark green leaf vein, whereas '22791-04' has an obtuse leaf apex, red purple flowers, and a dark red leaf vein. Additionally, 'PHALVAPYH' has shorter whiskers than '22791-04'.

'PHALVAPYH' differs from male parent plant '14261-01' (unpatented) in that 'PHALVAPYH' has an acute leaf apex, whereas '14261-01' has an obtuse leaf apex. Additionally, 'PHALVAPYH' has shorter whiskers than '14261-01'.

'PHALVAPYH' is most similar to the commercial *Phalaenopsis* plants named 'PHALANBL' (unpatented) and 'PHALAOYQ' (unpatented). 'PHALVAPYH' differs from the commercial variety 'PHALANBL' in that 'PHALVAPYH' has a change of color toward the center of the flower, a moderately elongated leaf base, red-purple whiskers, an acute leaf apex, and no lateral sepal pattern, whereas 'PHALANBL' has a flower pattern that is striped and dotted at the base, an elongated leaf base, purple-red whiskers, an obtuse to rounded leaf apex, and a lateral sepal pattern that is striped and dotted at the base. Additionally, 'PHALVAPYH' has shorter whiskers and larger flowers than 'PHALANBL'.

'PHALVAPYH' differs from the commercial variety 'PHALAOYQ' in that 'PHALVAPYH' has a change of color toward the center of the flower, a moderately elongated leaf base, red-purple whiskers, an acute leaf apex, weak curvature of the lateral lobe, and no lateral sepal pattern, whereas 'PHALAOYQ' has a striped flower pattern, an elongated leaf base, dark red whiskers, an obtuse leaf apex, medium curvature of the lateral lobe, and a lateral sepal pattern that is striped and dotted at the base. Additionally, 'PHALVAPYH' has longer whiskers and larger flowers than 'PHALAOYQ'.

I claim:

1. A new and distinct variety of *Phalaenopsis* plant named 'PHALVAPYH', substantially as described and illustrated herein.

* * * * *